(12) United States Patent
Abasolo et al.

(10) Patent No.: US 6,588,586 B2
(45) Date of Patent: Jul. 8, 2003

(54) MAILER FOR CELL CULTURE DEVICE

(75) Inventors: Nora Abasolo, Powell, OH (US); Rick D. Lucas, Galena, OH (US); Betsey Krause, Westerville, OH (US)

(73) Assignee: Biocrystal LTD, Westerville, OH (US)

( * ) Notice: Subject to any disclaimer, the term of this patent is extended or adjusted under 35 U.S.C. 154(b) by 0 days.

(21) Appl. No.: 09/788,972

(22) Filed: Feb. 20, 2001

(65) Prior Publication Data
US 2002/0069619 A1 Jun. 13, 2002

Related U.S. Application Data

(63) Continuation-in-part of application No. 09/732,676, filed on Dec. 8, 2000, now abandoned.

(51) Int. Cl.⁷ .............................................. B65D 81/26
(52) U.S. Cl. ...................... 206/204; 206/438; 229/68.1
(58) Field of Search .................. 53/449, 434; 206/204, 206/438, 439, 484.1, 570; 229/68.1; 422/102, 104

(56) References Cited

U.S. PATENT DOCUMENTS

| | | | |
|---|---|---|---|
| 3,809,223 A | * 5/1974 | Kendall | ...................... 206/204 |
| 4,240,547 A | 12/1980 | Taylor | |
| 4,657,804 A | * 4/1987 | Mays et al. | .................. 206/439 |
| 4,964,509 A | * 10/1990 | Insley et al. | ................. 206/204 |
| 5,199,795 A | * 4/1993 | Russo et al. | ................. 206/204 |
| 5,427,238 A | 6/1995 | Weiss | |
| 5,450,948 A | * 9/1995 | Beausoleil et al. | ......... 206/204 |
| 5,647,480 A | * 7/1997 | Insley et al. | ................. 206/204 |
| 5,697,200 A | * 12/1997 | Insley et al. | ................. 206/204 |
| 6,119,853 A | * 9/2000 | Garill et al. | ................. 206/204 |
| 2001/0050237 A1 | * 12/2001 | Hacikyan | .................... 206/204 |

* cited by examiner

Primary Examiner—Jim Foster
(74) Attorney, Agent, or Firm—Benesch, Friedlander, Coplan & Aronoff, LLP

(57) ABSTRACT

A mailer for shipping cells contained in a cell culture device, wherein the mailer comprises a containment system that can absorb and contain within the mailer a fluid that may leak from the cell culture device. The containment system comprises a gas-permeable absorbent material adapted to surround the cell culture apparatus; and a liquid impermeable layer which seals the absorbent material so as to contain any fluid released within the mailer.

22 Claims, 4 Drawing Sheets

MAILER FOR CELL CULTURE DEVICE

This is a continuation-in-part of copending application Ser. No. 09/732,676 filed on Dec. 08, 2000, abandoned, the disclosure of which is herein incorporated by reference.

FIELD OF THE INVENTION

The present invention relates to generally to shipping packages; and more particularly, to a mailer for shipping cultured cells.

BACKGROUND OF THE INVENTION

Genomics, proteomics, and drug discovery are generating a need for expanded versatility of applications for manipulating cell cultures, as well as a greater need for efficient and economical growth of cultured cells in high volume. Thus, the demand for cell lines for culturing is rapidly increasing. In medical and scientific research, it is frequently necessary to ship cell lines from one point to another via a mail carrier. The current standard procedure for shipping a cell line involves freezing the cells in a vial, packing the vial in dry ice inside a packaging container, and shipping the packaging container. There are several disadvantages to shipping with dry ice. First, particularly for smaller laboratories, it is often difficult to obtain dry ice on a regular basis. Additionally, dry ice is costly, and also adds to the net weight, and hence to the cost, of shipping. Also a concern, when shipping packages having packed therein fluid-containing containers, sometimes breakages and spillages can occur due to mishandling in transit between two locations. The requirement is for such package contents to be delivered intact; but if breakage does occur during transit, that the fluids within the package be properly contained within the package so as to avoid damaging other mail.

Thus, there is a need for a mailer for cell cultures, wherein the mailer makes more efficient use of package space, is less expensive with respect to packing materials and postage, and which contains a spillage of fluid in case breakage occurs during transit.

SUMMARY OF THE INVENTION

It is a primary object of the invention to provide a mailer for shipping cultured cells in a cell culture device via a mail carrier.

It is another object of the invention to provide a mailer for shipping cultured cells which is relatively more compact, lighter in weight, and less expensive than shipping the cells in dry ice.

It is another object of the present invention to provide a mailer for shipping a cell culture device, wherein the mailer provides a containment system which can absorb, and contain within the mailer, fluids that leak due to breakage of the cell culture device because of accidents during shipping.

It is yet another object of the present invention to provide a mailer for shipping a cell culture device, wherein the mailer has a containment system that comprises a large surface area of absorbent material that surrounds a cell culture device placed in the mailer for shipping, for absorbing fluids in the event of leakage of fluid from the cell culture device.

Briefly, the invention provides for a reusable mailer which is lightweight, enables a cell culture device to be inserted for shipping and readily removed upon receipt, completely encloses a cell culture device in a large surface area of absorbent material to absorb leaking fluid (cell culture medium or a fluid in which the cells may be stored during shipping) which may result from breakage during transit. Further containment of such fluid may be provided by placing the cell culture device into a pouch comprised of an absorbent material, wherein the pouch is lined on the exterior with a liquid-impermeable barrier; or by sealing the fluid and/or fluid-laden absorbent material comprising the housing material of the container using a liquid-impermeable barrier. More specifically, the mailer according to the present invention comprises: a housing comprised of a gas-permeable material, wherein the housing comprises a base section and a top panel, wherein the base section comprises a recess adapted for securely holding a cell culture device in place, and wherein the top panel is openable and closable with respect to the base section; and a gas-permeable absorbent material adapted to surround a cell culture device.

These and other objects and advantages of the invention will become more apparent from the following detailed description taken in conjunction with the accompanying drawings.

DETAILED DESCRIPTION OF THE INVENTION

Figure 1:
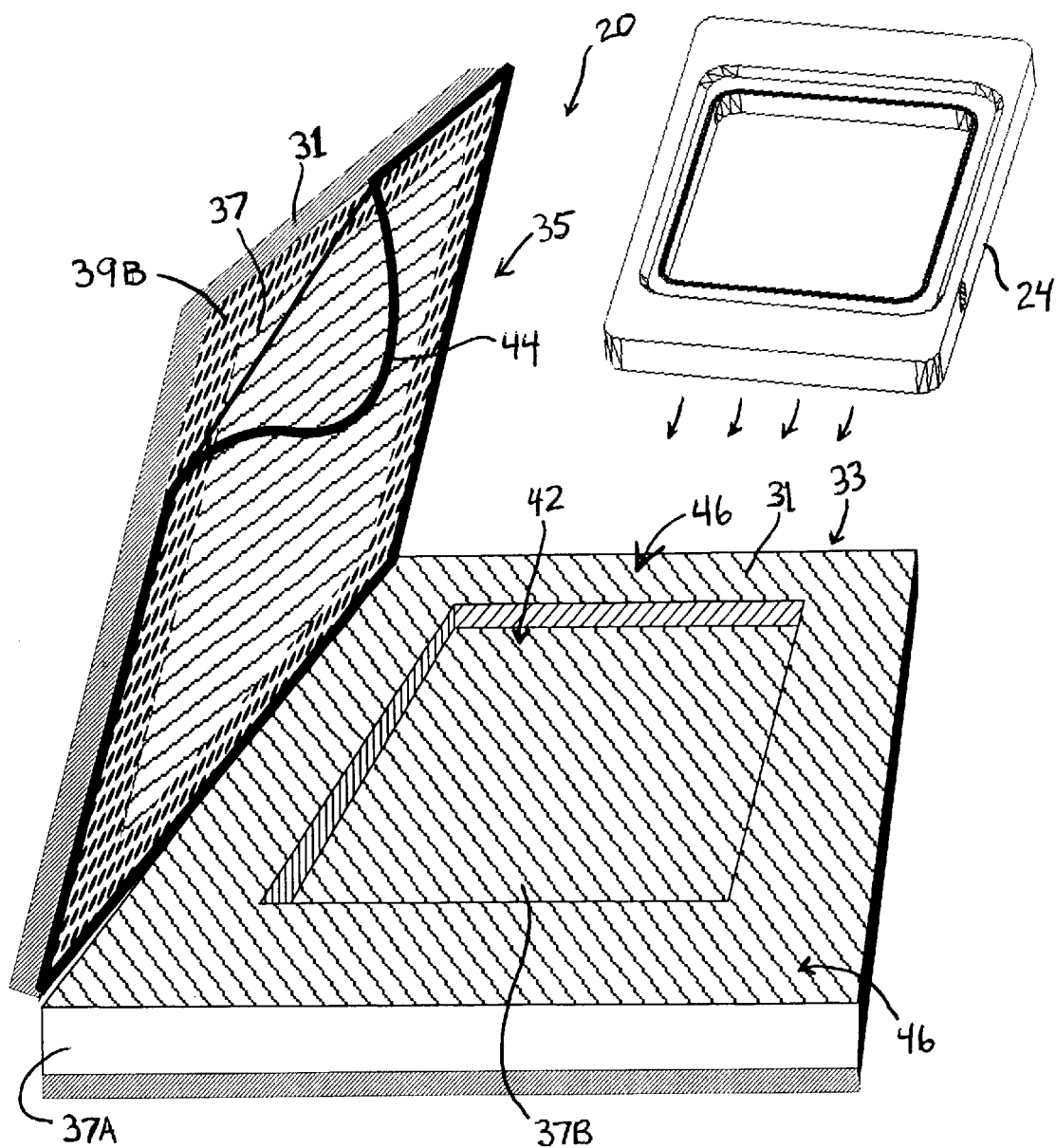
FIG. 1 is a perspective view of a first embodiment of the mailer according to the present invention for shipping a cell culture device.

In the embodiments of the mailer according to the present invention, inserted into the mailer for shipping is a cell culture device. The cell culture device to be used with the mailer according to the present invention is described in more detail in co-pending U.S. application Ser. Nos. 09/526,006, 09/724,251, and 09/724,153 (the disclosures of which are herein incorporated by reference). Briefly, the cell culture device is comprised of a frame to which is contacted and secured taut thereto, in a leak-proof sealing arrangement, at least one gas permeable, liquid impermeable membrane. In a preferred embodiment, two liquid impermeable membranes are secured thereto, wherein at least one of the membranes is gas-permeable; and more preferably, both membranes are gas permeable. Alternatively, there is one gas permeable, liquid impermeable membrane secured to the frame with the opposing surface comprising a rigid, clear plastic material typical of conventional cell culture containers (e.g., tissue culture flask and petri dish). The frame may be of a basic biocompatible composition that may comprise suitable plastic, thermoplastic, synthetic, or natural materials which can be fabricated into a framework structure, thereby achieving the required structural integrity for its intended purpose. In a further embodiment, the frame further comprises an identification code. An identification code comprises an identifier placed on or made a part of a frame, and which may include, but is not limited to, a bar code, a number, a series of numbers, a color, a series of colors, a letter, a series of letters, a symbol, a series of symbols, and a combination thereof. The identification code may be used for one or more of tracking, locating, identifying, identifying the position of (e.g., as relative to a point of origin), and cataloging the cell culture device (and the contents therein) having that identification code which is sought to be identified. While the identification code can be placed anywhere on the frame, preferably the identification code is placed on an edge of the frame. The culture chamber of the cell culture device, such as formed by the frame and two membranes, is accessed by at least one resealable access port which extends between the outer surface of the frame and the chamber. The gas permeable membrane is capable of allowing transfer of gases into and out of the culture chamber, and provides an attachment surface which promotes even distribution of anchorage dependent cells, spatial efficiency, and conditions which can promote a high rate of cell growth in achieving a high cell density in a relatively short period of time as compared to conventional cell culture devices. In a preferred embodiment, the cell culture device has a length in a range of from about 10 cm to about 13.5 cm, a width in a range of from about 7 cm to about 9 cm, and a height in a range of from about 0.2 cm to about 1.0 cm. In a most preferred embodiment, the cell culture device has a length of about 12.7 cm, a width of about 8.5 cm, and a height of about 0.58 cm.

As apparent to one skilled in the art, the cell culture device may contain (e.g., within the chamber of the cell culture device) cells, a fluid, and a combination thereof. Cells that may be contained in the cell culture device may comprise one or more cell types including, but not limited to, animal cells, insect cells, mammalian cells, human cells, transgenic cells, genetically engineered cells, transformed cells, cell lines, plant cells, anchorage-dependent cells, anchorage-independent cells, and other eukaryotic cells. The cells may also comprise cultured cells. The term "cultured cells" is used herein, for the purposes of the specification and claims, to mean one or more of: cells that are generally cultured as anchorage-dependent or as anchorage-independent; cells comprising cellular aggregates; an organized structure or network of cells in forming a tissue, as apparent to those skilled in the art. Cells cultured as either anchorage-dependent or anchorage-independent are known to those skilled in the art to include, but are not limited to, cell lines, tumor cells, hematopoietic cells, cells isolated from a tissue, or other cell type desired to be cultured (e.g., as readily available to, or can be isolated using standard techniques by, one skilled in the art). Cellular aggregates may be comprised of a single cell type or of multiple cell types; and, in culture, may further mimic one or more functions of a tissue or organ. As apparent to one skilled in the art from descriptions herein, tissue fragments may be introduced into the cell culture device of the in vitro system according to the present invention, and the tissue fragments themselves represent a tissue, or are cultured to form a tissue using methods known in the art. Alternately, a tissue may be engineered in the cell culture device by introduction into the cell culture device of the various cell types needed to form the tissue, using standard techniques known in the art (e.g., culturing cells on a three dimensional synthetic (e.g., polyglycolic acid) or natural (e.g., collagen or extracellular) matrix).

"Fluid" is used herein, for the purposes of the specification and claims, to mean a fluid comprising tissue culture medium, cell culture medium, a physiologically acceptable solution, or a combination thereof. The fluid may further comprise a substance secreted or excreted by cultured cells (e.g., antibody, cytokine, recombinant protein, and the like). As known in the art, a physiologically acceptable solution comprises a fluid, other than tissue culture medium or cell culture medium, known in the art for contacting cultured cells. As apparent to one skilled in the art, a physiologically acceptable solution may include, but is not limited to, a phosphate buffered salt solution (PBS), a balanced salt solution (e.g., Earle's or Hank's balanced salt solution, a balanced salt solution fortified with various nutrients, and the like). As known in the art, tissue culture medium refers to a liquid solution which is used to provide sufficient nutrients (e.g., vitamins, amino acids, essential nutrients, salts, and the like) and properties (e.g., osmolarity, buffering) to maintain living cells (preferably, eukaryotic cells) and support their growth. Various formulations of commercially available tissue culture medium are known to those skilled in the art. Cell culture medium is known in the art to refer to tissue culture medium that has been incubated or contacted with cultured cells; and more preferably refers to tissue culture medium that further comprises substances secreted or excreted by cultured cells as a result of culturing the cells in the presence of the tissue culture medium.

EXAMPLE 1

Figure 2:
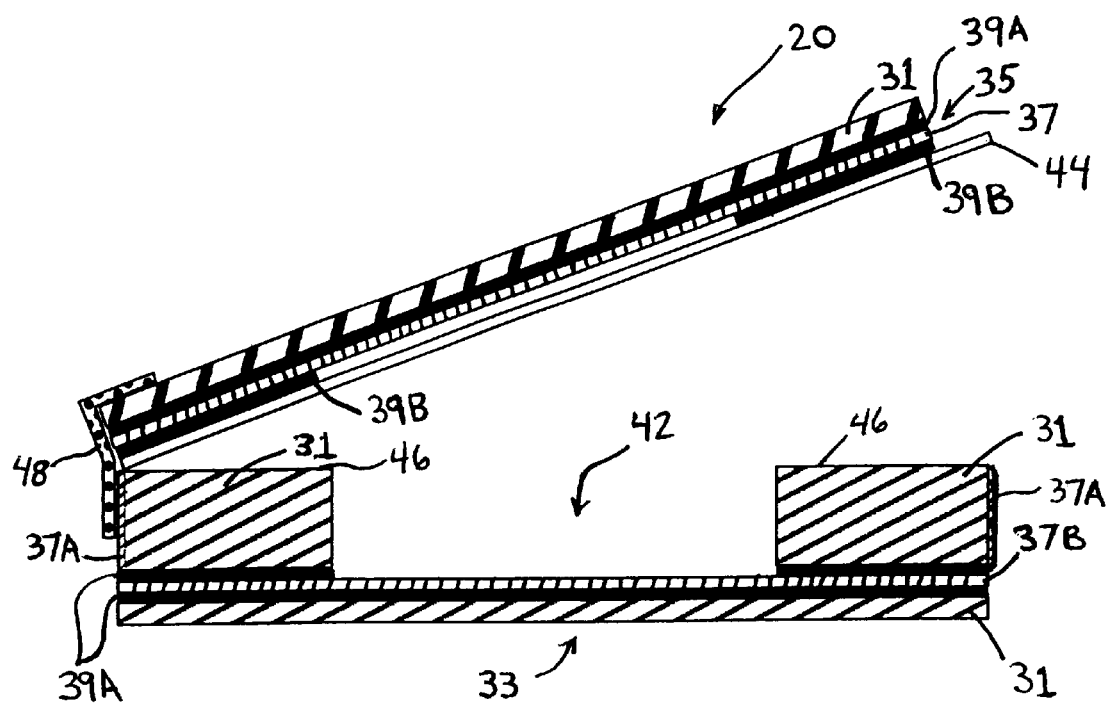
FIG. 2 is a cross-sectional view, taken width-wise, of the embodiment of the mailer illustrated in FIG. 1.

In a first embodiment of a mailer according to the present invention, and in referring to FIGS. 1–2, mailer 20 is comprised of: a rigid housing comprised of a gas-permeable, absorbent material 31 which has a base section 33 adapted to receive a cell culture device 24, and an openable and closable top panel 35; a liquid-impermeable layer (lining or coating the absorbent material) 37 adapted to seal fluids which have been absorbed by absorbent material 31; and liquid-impermeable, pressure sensitive adhesive 39. The mailer 20 may further comprise release liner 44 that extends over adhesive 39B on top panel 35. A containment system is formed within mailer 20 by: surrounding (e.g., encasing) the cell culture device contained therein with absorbent material 31; sealing such absorbent material 31 by lining the absorbent material (on the side opposite to that which faces the cell culture device) with a liquid-impermeable layer; and forming a leak-proof seal between closed top panel 35 and base section 33 by using non-permanent, liquid-impermeable, pressure sensitive adhesive 39B. Preferably, via the containment system, a leak-proof closure of the mailer interior is obtained.

Absorbent material 31 is substantially rigid to provide the desired structural integrity for its intended purpose as a shipping container; e.g., retains its integrity during typical shipping and handling procedures, and thereby protects the cell culture device enclosed therein from breaking. The absorbent material may be comprised of a material including, but not limited to, a natural cellulosic material, and a non-natural (e.g., manufactured) cellulosic material, known to those skilled in the art. Such materials are generally considered lightweight with respect to shipping costs. The absorbent material may be of a single construction or multi-ply form. Exemplary absorbent materials may comprise one or more of paperboard, cardboard, cellulosic fiberboard, and a rigid material formed of wet-strong long fibers (e.g., cellulosic fibers, each having a length of about 10 cm in its natural state). Preferably, the absorbent material is biodegradable (normal disposal) and combustible (if desired to be incinerated). In a preferred embodiment, the absorbent material has the absorbing capacity of at least two (2), and more preferably greater than three (3), times the maximum volume of liquid (e.g., fluid) capacity of the cell culture device to be enclosed therein for shipping. As apparent to one skilled in the art, that fluid capacity will depend on the dimensions of the cell culture device.

Absorbent material 31 of base section 33 is configured to so as to form recess 42 that is adapted to snugly receive cell culture device 24 in permitting cell culture device 24 to be readily inserted or removed. For example, where the dimensions of the cell culture device to be shipped comprise a length of about 12.5 cm, a width of about 8.5 cm, and a height of about 0.58 cm (with a maximum fluid capacity of about 10 ml), the dimensions of recessed area may comprise a length of about 12.8 cm, a width of about 8.7 cm, and a depth of about 0.6 mm. However, the dimensions may be varied depending on the user's needs. For example, in another embodiment, one or more additional sheets of an absorbent material (e.g., for extra cushioning and/or absorbent function) may be added to the mailer, and placed in contact with the cell culture device, before sealingly enclosing the cell culture device in the mailer. For example, one or more sheets of absorbent material may be formed to fit the bottom of the recess so as to be positioned between an inserted cell culture device and the liquid impermeable layer. Additionally, or in the alternative, one or more sheets of absorbent material may be formed to fit the recess and to overlay an inserted cell culture device so as to be positioned between an inserted cell culture device and the top panel without interfering with the closure of top panel 35 and its being sealing secured to base section 33.

In referring to FIG. 2, lining the bottom of recess 42, and along the exterior walls of the absorbent material 31 that forms recess 42, is liquid-impermeable layer 37. With this arrangement, leakage of fluids in the recess is confined to the recess and surrounding absorbent material. Preferably, liquid-impermeable layer 37 is gas permeable. Materials that are liquid-impermeable and gas-permeable, and that may be assembled as a layer or applied as a coating (e.g., by spray or roller), are known in the art to include, but are not limited to, polystyrene, polyethylene, polycarbonate, polyolefin, ethylene vinyl acetate, polypropylene, polysulfone, polytetrafluoroethylene, a silicone copolymer, and other suitable polymers. For example, and in continuing reference to FIG. 2, liquid impermeable layer 37A may comprise a sealing coating over absorbent material 31; and liquid impermeable layer 37B may comprise a sheet that is adhesively secured to absorbent material by use of a permanent, liquid-impermeable, pressure sensitive adhesive 39A. A "permanent" adhesive has a well known, art recognized meaning to describe an adhesive which forms a strong bond with a substrate to which it is applied, so that neither the adhesive nor the material to which it is applied can be removed without damaging it. "Pressure sensitive" has a well known, art recognized meaning to describe an adhesive which quickly bonds when contact pressure is applied to force the adhesive to contact the substrate; e.g., sufficient tack to adhere to a substrate using only light pressure, such as the amount of pressure administered with a hand. Conventional permanent, liquid impermeable, pressure sensitive adhesives are well known in the art to include, but are not limited to, acrylic-based adhesives, and rubber-based adhesives.

As illustrated in FIGS. 1–2, a non-permanent, liquid-impermeable, pressure sensitive adhesive 39B may be used for sealing and detachably securing top panel 35 to base section 33. In a preferred embodiment, non-permanent, liquid-impermeable, pressure sensitive adhesive 39B is placed around substantially all of the surface area adjacent to the edges of top panel so that, upon closure of the top panel and in contacting the bottom section, adhesive 39B binds outward face 46 of the absorbent material that surrounds the opening of the recess in forming a leak-proof seal. A "non-permanent" adhesive has a well known, art recognized meaning to describe an adhesive which can be peeled off, together with the material onto which it is applied, from the substrate without damage to either the non-permanent adhesive or the substrate. Conventional liquid impermeable, pressure sensitive, non-permanent adhesives are well known in the art to include, but are not limited to, synthetic or natural rubber-based adhesive compositions, and acrylic-based adhesive compositions. In a preferred embodiment, release liner 44 is provided as a sheet or as a strip to protect adhesive 39B prior to detachably securing top panel 35 to base section 33. Release liner 44 protects the adhesive surface from collecting lint or dust or binding to a substrate which it is not intended to be adhered. A release liner, as known in the art, has a surface that is not very adherable by the adhesive which it covers, and thus is very releasable from the adhesive. Typical release liners are a paper or polymer film which may be coated with a release coating. Examples of release liner materials include, but are not limited to, paper, polyethylene-coated paper, polyethylene film, polyester film, polyvinyl film, polypropylene film, and the like. Release coatings may include, but are not limited to, a silicon compound such as a silanol-stopped dimethylpolysiloxane, or dimethylvinyl-stopped dimethylpolysiloxane.

Top panel 35 and base section 33 may be hinged together, along an edge of the top panel which is aligned with an abutted edge of the base section, and with hinge means 48 comprising a flexible tape or other hinge means to provide the opening and closing transitional movements during use. In an alternative, top panel 35 and base section 33 may be integrally formed, and hinge means 48 may comprise a fold line and/or scored with score lines provided in the material used to form the top panel and base section. The mailer according to the present invention may further comprise a side pocket (e.g., formed by adhering a plastic pouch using a tape or adhesive) which may be secured on an exterior surface of either the top panel or base section, and into which may be placed one or more of a shipping receipt, shipping information, and information about the cells being shipped (e.g., type of cells, growth conditions, and the like).

A method for using the mailer according to the present invention comprises inserting a cell culture device containing cells, a fluid, or a combination thereof (e.g., cells and a fluid preferably comprising tissue culture medium, cell culture medium, or other suitable fluid for maintaining the viability of cells during the transit period) into the recess; removing the release liner from the non-permanent, liquid-impermeable, pressure sensitive adhesive (e.g., by peeling off the release liner so as to expose the non-permanent adhesive); and closing the top panel to contact the base section to seal and detachably secure top panel to base section. The method may further comprise placing the sealed mailer according to the present invention into a mailing envelope (e.g., paper or cardboard) upon which is placed the mailing address and postage, sealing the envelope having the mailer inside, and mailing the envelope to the mailing address. When received, the mailing addressee may open the mailer by grasping the top panel, and opening the top panel by applying sufficient force to overcome the non-permanent adhesive contact between the top panel and base section; and may then remove the cell culture device from the recess of the mailer.

It will be apparent to one skilled in the art, that the mailer according to the present invention may be expanded to have two or more recesses in having the capacity to hold more than one cell culture device. Thus, "a cell culture device" may be also viewed as plural when the mailer is constructed to accommodate more than one cell culture device.

EXAMPLE 2

Figure 3:
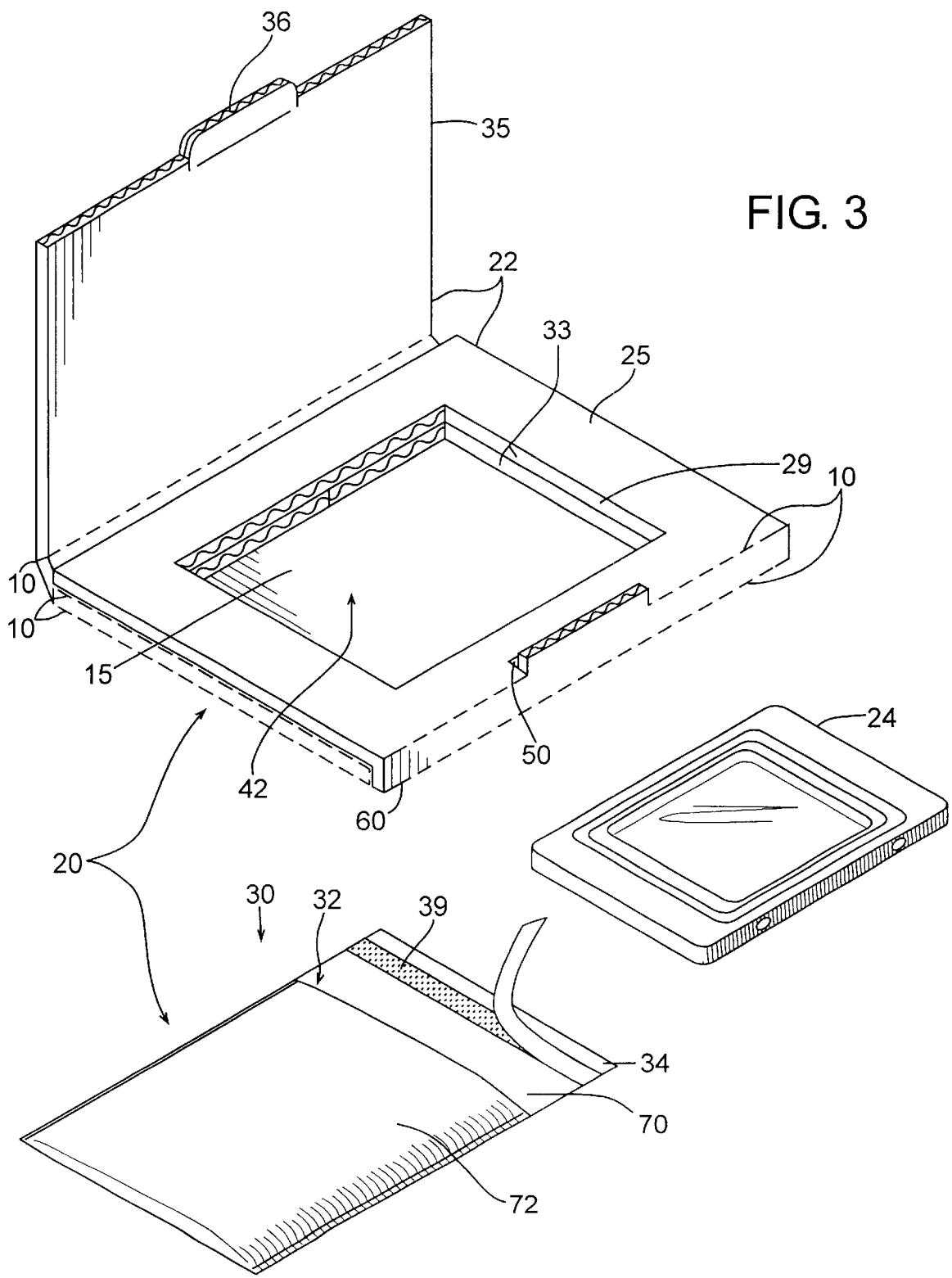
FIG. 3 is a perspective view of an embodiment of the mailer according to the present invention for shipping a cell culture device.
Figure 4:
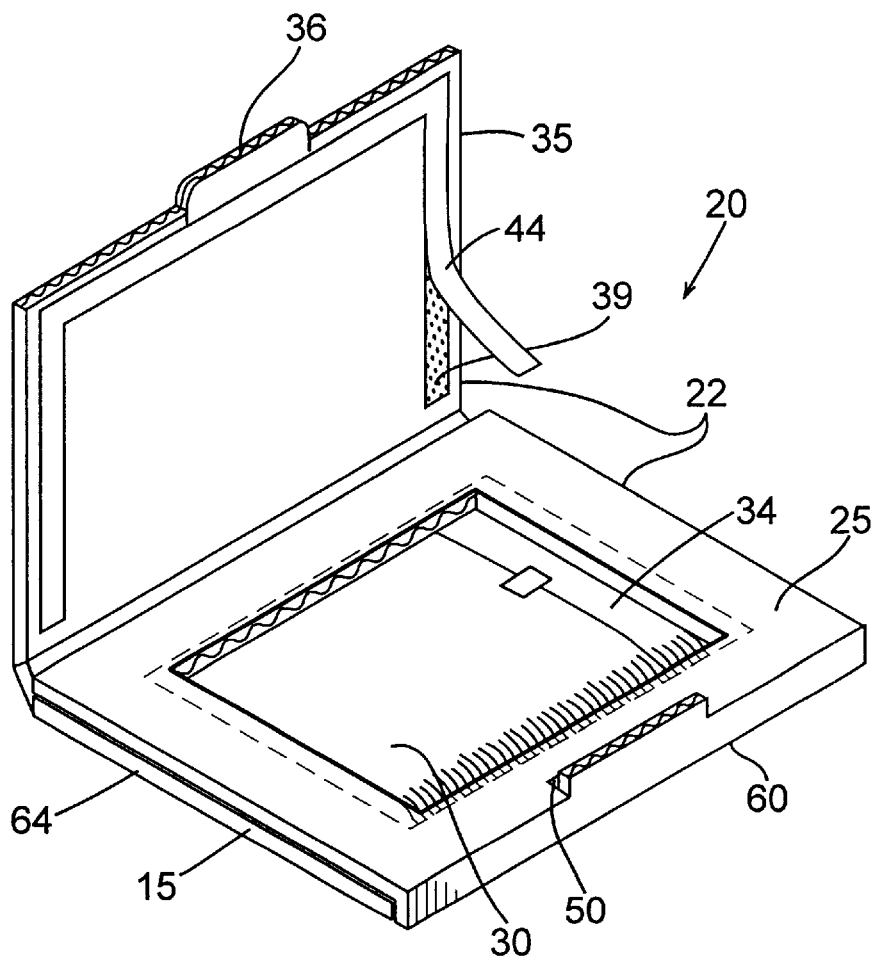
FIG. 4 is a perspective view of another embodiment of a mailer according to the present invention showing the mailer, containing a cell culture device, in an open position.

In referring to FIGS. 3–4, provided is mailer 20 comprised of a housing comprising shipping container 22, and pouch 30. Shipping container 22 may be constructed of paperboard, cardboard, a relatively thin corrugated cardboard, or similar material which is gas-permeable (e.g., is breathable by allowing air to diffuse through the material), and which provides the structural rigidity necessary for the protected shipment of the contents therein. Shipping container 22 is preferably made of a single sheet, and preferably of relatively thin corrugated cardboard. The single sheet may be fabricated by die cutting, or a cutting operation in a manner which is well known in the packaging industry; and may further be processed (e.g., to form fold lines and/or scored with score lines) to facilitate folding to form the shipping container. Shipping container 22 comprises three generally rectangular panels: a center panel 15, and an end panel 25 having a rectangular opening (window cut-out) 29, which together, when the single sheet is folded to form the shipping container, comprise a base section 33 having a recess 42 which is adapted to snugly fit pouch 30 containing cell culture device 24 to be securely held in position in the mailer; and an end panel, with at least one locking tab 36, which, when the single sheet is folded to form the shipping container, comprises top panel 35. In a preferred embodiment, shipping container 22 has a plurality of score lines 10 which facilitate one or more of: folding the single sheet to form the shipping container; or to provide a hinge function in allowing movement of top panel 35 in a process of opening or closing of shipping container 22. For example, a hinge means to hinge top panel and base section together may comprise a fold line, score lines, and a combination thereof.

Figure 5:
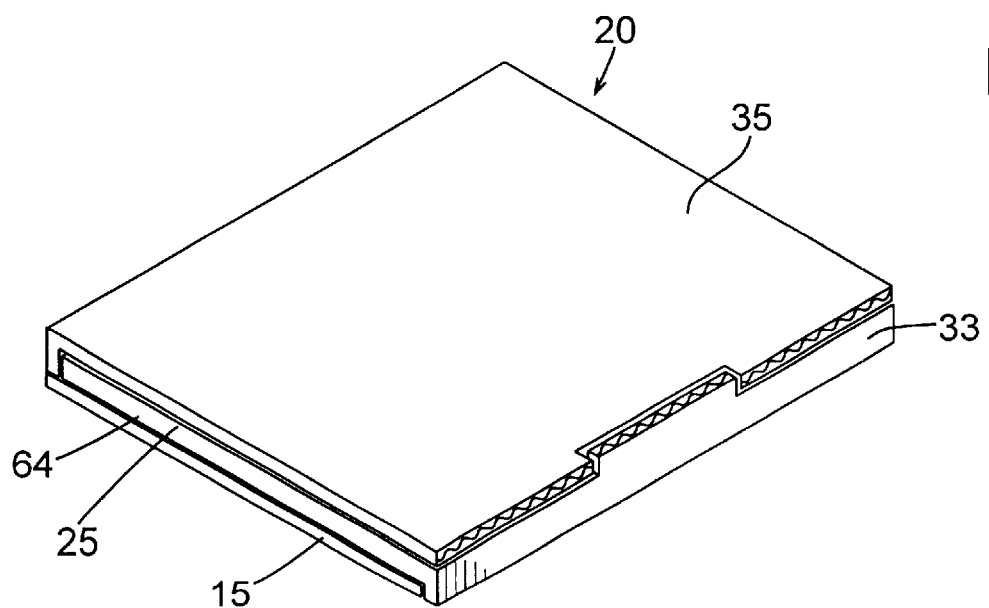
FIG. 5 is a perspective view of the mailer according to the present invention showing the mailer, containing a cell culture device, securely closed.

Top panel 35 comprises at least one locking tab 36, wherein each locking tab is a sufficient length to be received by, and is snugly received by, a slot 50 which is formed in the shipping container in securing the top panel in a closed position when securely closing the mailer. While FIGS. 3–5 show a preferred embodiment wherein locking tab 36 is snugly received by slot 50 formed along an edge adjacent to end panel 25, it will be apparent to one skilled in the art that a slot 50 may also be positioned in an alternate position; e.g., formed along edge 60 adjacent to base section 33 which forms a hinge between end panel 25 and center panel 15. In another embodiment as illustrated in FIG. 4, and similar to an embodiment previously described herein, top panel 35 may further comprise a pressure sensitive, non-permanent adhesive 39 applied along its edges which, when the top panel is closed to contact base section 33, the top panel is detachably secured to the base section in arranging the mailer in a closed position. A conventional release liner 44 may be used to cover adhesive 39 until the top panel 35 is ready to be secured to base section 33 (i.e., release liner 44 is removed to reveal the underlying adhesive 39, and then top panel 35 may be pressed against base section 33 to detachably secure top panel 35 to base section 33).

As apparent from FIGS. 4–5, base section 33 may comprise extensions comprising hinged (e.g., by fold lines, scoring lines, other hinged means, or a combination thereof) end flaps 64 located on parallel and opposing sides of base section 33. In one embodiment, as illustrated in FIG. 4, hinged end flaps 64 are formed as part of the center panel 15, and extend upwardly and adjacent to end panel 25 so as to be disposed between the center panel 15 and end panel 25 (in contacting end panel 25) in forming recess 42, base section 33, and shipping container 22. If desired, surfaces of hinged end flaps 64 and the surface of end panel 25 which come in contact may be further secured together by an adhesive disposed therebetween. In an alternative example, end panel 25 may comprise extensions comprise hinged end flaps 64 which are extended downward and adjacent to center panel 15 so as to be disposed between center panel 15 and end panel 25 (in contacting center panel 15) in forming recess 42, base section 33, and shipping container 22. If desired, surfaces of hinged end flaps 64 and the surface of center panel 15 which come in contact may be further secured together by an adhesive disposed therebetween. The depth of recess 42 may be controlled by the dimensions of the ends of the shipping container formed by the folded, hinged end flaps 64. Preferably, and as illustrated in FIG. 4, the depth of recess 42 is selected to be approximately equal to or slightly greater than the thickness of pouch 30 having enclosed therein cell culture device 24 when the pouch is snugly held into position in mailer 20. In a preferred embodiment, the depth of recess 42 is in the range of from about 6 mm to about 10 mm. Additionally, the width and length of recess 42 is selected to be approximately equal to or slightly greater than the width and length of pouch 30 containing cell culture device 24, so as to snugly hold pouch 30 into position in mailer 20. For example, where the dimensions of cell culture device 24 to be shipped comprise a length of about 12.5 cm, a width of about 8.5 cm, the dimensions of recess 42 may comprise a length in the range of about 13.4 cm to about 14 cm, and width in the range of about 9 cm to about 9.7 cm. However, the dimensions may be varied depending on the user's needs, the size of the cell culture device, and the size of the pouch (including thickness of the absorbent material comprising the pouch). As relative to the user's need, it may be desirable to leave enough room in recess 42 to include one or more folded sheets of printed paper in the mailer, wherein the printed paper may comprise product information, shipping information, billing information, and a combination thereof.

Pouch 30 forms a containment system comprising a leak-proof enclosure formed around a cell culture device 24 which is enclosed therein. Pouch 30 is comprised of a gas-permeable absorbent material 70 (adapted to surround a cell culture device) having a waterproof (e.g., liquid-impermeable) backing 72. The absorbent material may be of a single construction or multi-ply form, and may be of a material that is typically found in absorbent pads. Preferably, the absorbent material is biodegradable (normal disposal) and combustible (if desired to be incinerated). In a preferred embodiment, the absorbent material has the absorbing capacity of at least two (2), and more preferably greater than three (3), times the maximum volume of liquid (e.g., fluid) capacity of the cell culture device to be enclosed therein for shipping. In a more preferred embodiment, the absorbent material can absorb at least 750 ml, and more preferably greater than 1,000 ml, of fluid per square meter of absorbent material. As known to those skilled in the art, the absorbent material may include, but is not limited to, highly absorbent paper cloth, a material comprised of wet-strong long fibers (e.g., cellulosic fibers, each having a length of about 10 cm in its natural state), and the like. In a preferred embodiment, the absorbent material is non-abrasive so as to avoid scratching of transparent surfaces of cell culture device 24 when enclosed in pouch 30. A preferred absorbent material having a waterproof backing is available commercially as VERSI- DRY®. The waterproof backing (or layer) comprises a material that is liquid-impermeable and gas-permeable that is known in the art to include, but is not limited to, polystyrene, polyethylene, polycarbonate, polyolefin, ethylene vinyl acetate, polypropylene, polysulfone, polytetrafluoroethylene, a silicone copolymer, and other suitable polymers. A preferred absorbent material has a polyethylene backing. It will be appreciated by those skilled in the art, and with reference to FIG. 3, that waterproof backing 72 forms the exterior surface of pouch 30, and that absorbent material 70 comprises the interior walls defining the interior compartment of pouch 30 in forming the containment system (i.e., any fluid released inside the pouch will be absorbed by the absorbent material but be prevented from passing through the water-proof backing). Pouch 30 also provides cushioning, during the shipment of mailer 20, to help protect cell culture device 24 enclosed therein.

Pouch 30 has an opening 32 and a flap 34 adjacent to opening 32. After cell culture device 24 has been inserted through opening 32 into pouch 30, flap 34 is provided for securely closing pouch 30 in enclosing cell culture device 24 therein and restraining it from moving out of pouch 30. Securely closing pouch 30 may be achieved by either tucking flap 34 into opening 32 and over cell culture device 24, or otherwise by securing flap 34 over opening 32 of pouch 30. In tucking flap 34 into opening 32 and over cell culture device 24, flap 34 is of sufficient length to extend into pouch 30 in forming a lid for the pouch; and pouch 30 will be prevented from unraveling (in maintaining the enclosure around the cell culture device, and while retaining the cell culture device within the closed pouch) by it being snugly fit into shipping container 30 in forming mailer 20 in a closed position. If desired, applied onto the exterior surface (the water proof backing) of flap 34 or onto an interior surface of the pouch which comes in contact with tucked in flap 34 may be a pressure sensitive, non-permanent adhesive 39 with release liner 44. By removing the release liner, in tucking flap 34 into pouch 30, the pressure sensitive non-permanent adhesive may be used to detachably secure tucked in flap 34 to the absorbent material comprising an interior surface of the pouch in detachably securing the flap in a closed position. In another embodiment, flap 34 is of a sufficient length that it may be folded over opening 32 in forming a lid for the pouch, wherein a portion of the flap (e.g., a distal end) may then be detachably secured to the exterior surface 72 of pouch 30. Detachably securing the flap to the exterior surface provides a means to secure the flap in maintaining the pouch in a closed position, and to allow for opening 32 to be opened by releasing the flap 34 from being secured to pouch 30. In that regard, flap 34 may be detachably secured to the exterior surface of pouch 30 by a pressure sensitive, non-permanent adhesive 39, and may further comprise a release liner 44 to be removed from the adhesive before the flap is detachably secured to the exterior surface. The adhesive may be applied as a strip along the flap (see, e.g., FIG. 3) or, or as a tab (e.g., in the form of tape) that is adhered to both the flap and exterior surface (see, e.g., FIG. 4).

Absorbent material with the waterproof backing may be folded to form pouch 30, wherein adjacent edges of the material, other than at opening 32, may be sealed together in a leak-proof sealing to form pouch 32. The leak-proof sealing may be achieved by sealing adjacent edges together using a means which may include, but is not limited to, sewing, bonding (e.g., heat sealing or use of an adhesive), or other suitable means known to those skilled in the art. The dimensions of the interior compartment of pouch 30 are selected to be approximately equal to or slightly greater than the dimensions of cell culture device 40 to be snugly received by and enclosed in pouch 30. For example, where the dimensions of the cell culture device to be shipped comprise a length of about 12.5 cm, a width of about 8.5 cm, and a height of about 0.58 cm, the dimensions of the interior compartment of the pouch may comprise a length of in a range of about 13.5 cm to about 14.0 cm, and a width of about 10 cm to about 10.5 cm. In that regard the length of flap 34 for securely closing pouch 30 may be in a range of about 3 cm to about 5 cm. However, the dimensions of pouch 30 may be varied depending on the user's needs, the size of the cell culture device, and the size of recess 44.

Mailer 20 according to the present invention may further comprise one or more of a mailing label (to identify the addressee, and may further identify the sender); or a side pocket (e.g., formed by adhering a plastic pouch using a tape or adhesive) which may be secured on the closed mailer on an exterior (outward facing) surface of either the top panel or base panel section, and into which may be placed one or more of a shipping receipt, shipping information, and information about the product being shipped (e.g., type of cells, growth conditions, and the like).

A method for using the mailer according to the present invention comprises: inserting a cell culture device, containing tissue culture medium (or other suitable fluid for maintaining the cells during the transit period) and cells, into the pouch; securely closing the pouch so as to enclose the cell culture device within the closed pouch; placing the securely closed pouch into the recess of the shipping container in forming the mailer; and securely closing the mailer by securing, in a closed position, the top panel of the shipping container. The method may further comprise placing the securely closed mailer according to the present invention into a mailing envelope (e.g., paper or cardboard) upon which is placed the mailing address (and may further require postage placed thereon), sealing the envelope having the mailer inside, and mailing the envelope to the mailing address, in accordance with the particular mail carrier's regulations. When received by the mailing addressee, the mailing addressee may open the mailer by grasping the top panel, and opening the top panel by removing the locking tab from the slot into which the locking tab was inserted. Where the top panel further comprises a pressure sensitive, non-permanent adhesive, the mailing addressee will additionally need to apply sufficient force to overcome the non-permanent adhesive contact between the top panel and the end panel to which it is detachably secured. The pouch may then be removed from the recess of the shipping container, and the flap of the pouch is then unfolded so that the enclosed cell culture device may be pulled out through the pouch opening in removing the cell culture device from the pouch.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A mailer for shipping a cell culture device, the mailer comprising:
    (a) a housing comprised of a gas-permeable material, wherein the housing comprises a base section and a top panel, wherein the base section comprises a recess adapted for securely holding a cell culture device, and wherein the top panel is openable and closable with respect to the base section;

(b) a gas-permeable absorbent material adapted to surround a cell culture device; and (c) a liquid impermeable, gas-permeable layer for sealing the absorbent material.

2. The mailer according to claim 1, further comprising a cell culture device securely held by the recess.

3. The mailer according to claim 2, wherein the cell culture device further comprises a component selected from the group consisting of cells, a fluid, and a combination thereof.

4. The mailer according to claim 1, wherein the housing comprises the gas-permeable absorbent material.

5. The mailer according to claim 1, wherein the gas-permeable absorbent material comprises a pouch.

6. The mailer according to claim 1, further comprising a means to detachably secure the top panel to the base section selected from the group consisting of at least one locking tab, a pressure sensitive non-permanent adhesive, and a combination thereof.

7. The mailer according to claim 6, wherein the means to detachably secure the top panel to the base section comprises a pressure sensitive, non-permanent adhesive.

8. The mailer according to claim 7, further comprising a release liner which is detachably secured to the pressure sensitive, non-permanent adhesive.

9. The mailer according to claim 7, wherein the pressure sensitive non-permanent adhesive is liquid impermeable.

10. The mailer according to claim 1, wherein the absorbent material has the absorbing capacity of greater than 3 times the maximum fluid volume of the cell culture device.

11. The mailer according to claim 1, wherein the top panel and base section are hinged together by a hinge means selected from the group consisting of flexible tape, score lines, a fold line, and a combination of a fold line and score lines.

12. The mailer according to claim 1, wherein the mailer further comprises a side pocket secured to an exterior surface of the mailer.

13. A mailer for a cell culture device, comprising:

a containment system that can absorb and contain within the mailer a fluid that may leak from the cell culture device, the containment system including a gas-permeable absorbent material adapted to surround a cell culture device, and a liquid impermeable, gas-permeable layer for sealing the absorbent material so as to contain the fluid within the mailer; and a pouch comprised of the gas-permeable absorbent material; wherein the pouch comprises an opening through which the cell culture device may be inserted, and a flap for opening and closing the pouch; and wherein the pouch may be securely closed by a means selected from the group consisting of tucking the flap into the opening, folding the flap over the opening and using a pressure sensitive non-permanent adhesive to secure the flap to a surface the pouch, and tucking the flap into the opening and using a pressure sensitive non-permanent adhesive to secure the flap to a surface of the pouch.

14. A mailer for shipping a cell culture device, the mailer comprising:

(a) a housing comprised of a gas-permeable absorbent material adapted to surround a cell culture device held into place in the mailer, wherein the housing comprises a base section and a top panel, wherein the base section comprises a recess adapted for securely holding a cell culture device, wherein the top panel is openable and closable with respect to the base section, and;

(b) a liquid impermeable, gas-permeable layer for sealing the absorbent material;

(c) a liquid impermeable, pressure sensitive non-permanent adhesive adapted to detachably secure the top panel to the base section.

15. The mailer according to claim 14, wherein the absorbent material has the absorbing capacity of greater than 3 times the maximum fluid volume of the cell culture device.

16. The mailer according to claim 14, wherein the top panel and base section are hinged together by a hinge means comprising flexible tape.

17. The mailer according to claim 14, further comprising a release liner which is detachably secured to the pressure sensitive, non-permanent adhesive.

18. A method of using the mailer according to claim 17, the method comprising: inserting a cell culture device into the recessed area; removing the release liner from the liquid impermeable, pressure sensitive non-permanent adhesive; and closing the top panel to contact the base section to seal and detachably secure the top panel to the base section.

19. A mailer for shipping a cell culture device, the mailer comprising:

(a) a shipping container comprised of a gas-permeable material, wherein the shipping contanier comprises a base section and a top panel, wherein the base section comprises a recess adapted for securely holding a pouch containing a cell culture device, and wherein the top panel is openable and closable with respect to the base section;

(b) a means to detachably secure the top panel to the base section selected from the group consisting of at least one locking tab, a pressure sensitive non-permanent adhesive, and a combination thereof; and (c) a pouch comprised of a gas-permeable absorbent material having a liquid impermeable, gas-permeable backing, wherein the pouch is adapted to surround a cell culture device with the gas-permeable absorbent material, wherein the pouch comprises an opening through which the cell culture device may be inserted, and a flap for opening and closing the pouch; and (d) a means for securely closing the pouch selected from the group consisting of tucking the flap into the opening, folding the flap over the opening and using a pressure sensitive non-permanent adhesive to secure the flap to a surface of the pouch, and tucking the flap into the opening and using a pressure sensitive non-permanent adhesive to secure the flap to a surface of the pouch.

20. The mailer according to claim 19, wherein the absorbent material has the absorbing capacity of greater than 3 times the maximum fluid volume of the cell culture device.

21. The mailer according to claim 14, wherein the top panel and base section are hinged together by a hinge means comprising a fold line and score lines.

22. A method of using the mailer according to claim 19, the method comprising: inserting a cell culture device through the opening of the pouch and into the pouch; securely closing the pouch so as to enclose the cell culture device within the closed pouch; placing the securely closed pouch into the recess of the shipping container in forming the mailer; and closing the top panel to contact the base section, and detachably securing the top panel to the base section in closing the mailer.

* * * * *